United States Patent [19]
Johnson et al.

[11] Patent Number: 6,012,181
[45] Date of Patent: Jan. 11, 2000

[54] SYSTEM FOR DRAINING A URINARY DRAINAGE CONTAINER

[75] Inventors: Wayne H. Johnson, Ham Lake; Kevin D. Murphy, Elko, both of Minn.

[73] Assignee: Quality Assistive Devices, Incorporated, Ham Lake, Minn.

[21] Appl. No.: 09/131,945

[22] Filed: Aug. 10, 1998

[51] Int. Cl.⁷ .................................................. A47K 11/06
[52] U.S. Cl. .................. 4/480; 4/144.1; 604/323
[58] Field of Search ............... 4/144.1, 254, 480; 604/323, 335

[56] References Cited

U.S. PATENT DOCUMENTS

| | | | |
|---|---|---|---|
| 3,931,650 | 1/1976 | Miller | 4/480 |
| 3,964,786 | 6/1976 | Mashuda | 297/330 |
| 4,532,936 | 8/1985 | LeVeen et al. | 604/323 X |
| 4,631,061 | 12/1986 | Martin | 604/323 X |
| 4,718,689 | 1/1988 | Lott | 604/326 X |
| 4,861,059 | 8/1989 | Shirk | 280/304.1 |
| 4,888,005 | 12/1989 | Dingeman et al. | 604/326 |
| 5,397,315 | 3/1995 | Schmidt et al. | 604/323 |
| 5,466,229 | 11/1995 | Elson et al. | 604/323 X |
| 5,577,753 | 11/1996 | Pociask | 280/250.1 |
| 5,584,826 | 12/1996 | Faenger et al. | 604/322 |

OTHER PUBLICATIONS

One page of a spec sheet for a valve sold by Parker Hannifin Corporation of Jacksonville, Alabama (date unknown).
R.D. Equipment, Inc., "The original "Electric Leg Bag Emptier" Complete Independence!", 2 pgs., © 1996.

*Primary Examiner*—Robert M. Fetsuga
*Attorney, Agent, or Firm*—Merchant & Gould P.C.

[57] ABSTRACT

An improved system that allows a disabled person in a wheelchair to automatically empty the contents of a bodily waste collection receptacle, such as a leg bag, without the aid of an attendant. The system comprises a pump mounted on the wheelchair, with the pump having an inlet port and a discharge port. The inlet port is connectable to the drain tube of the collection receptacle, and a discharge line is connected to the discharge port of the pump. The discharge line is mounted on the wheelchair, and a valve is provided which controls flow through the discharge line. The valve is selectively positionable between an open position in which flow is permitted through the discharge line and a closed position in which flow is prevented through the discharge line.

23 Claims, 3 Drawing Sheets

FIG. 2
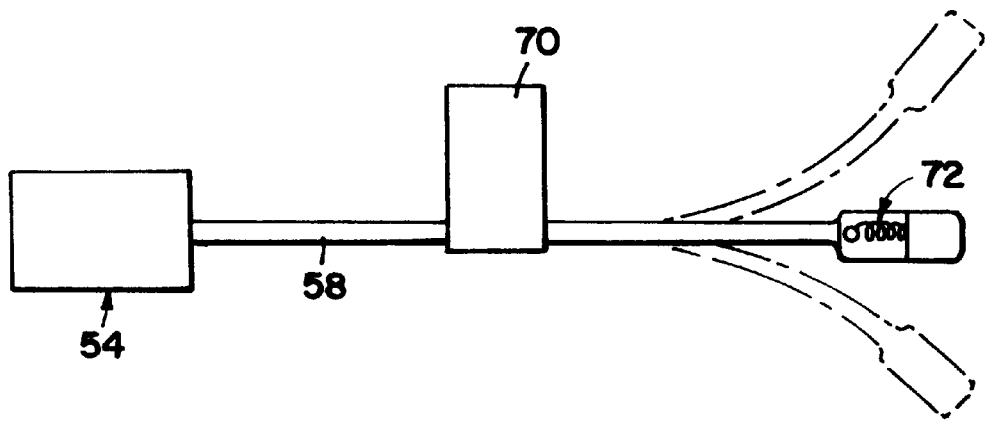
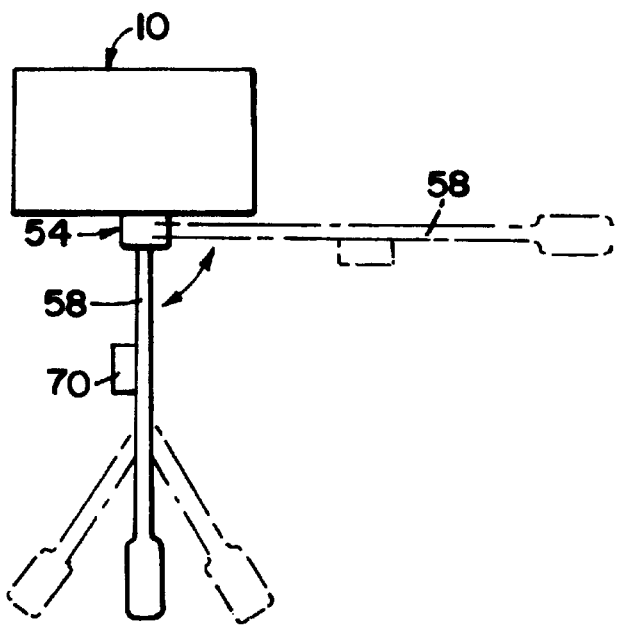
FIG. 3

SYSTEM FOR DRAINING A URINARY DRAINAGE CONTAINER

FIELD OF THE INVENTION

The invention relates to urine collection devices, and more specifically to leg bags which are utilized by persons confined to wheelchairs. More particularly, the invention relates to a system for allowing an occupant of wheelchair to automatically empty a leg bag without the aid of an attendant or assistant.

BACKGROUND OF THE INVENTION

Many types of people with disabilities use urine collection receptacles called leg bags in order to collect their urine. In a conventional leg bag, a drain tube is connected to the bag to permit emptying of the leg bag. Emptying of a leg bag is a frequent requirement because paraplegic and quadriplegic patients excrete exceptional amounts of urinary waste to compensate for deficiencies in other excretory processes. For paraplegic and quadriplegic patients in particular, this operation poses an enormous problem, due to limited mobility which prevents them from emptying the leg bag themselves. The assistance of an attendant or assistant is therefore required in order to empty the leg bag, thereby reducing the independence of the disabled person and may at times cause embarrassment for the individual.

An attempt to resolve this problem is disclosed in U.S. Pat. No. 3,931,650 to Miller. Miller discloses an apparatus which allows unassisted emptying of a leg bag by the occupant of the wheelchair. The apparatus includes a valve that is attached to the wheelchair, and which has an inlet that is connected to the drain tube of the leg bag. The outlet of the valve is connected to outlet tubing disposed beneath the wheelchair. The valve is manually actuatable by the occupant of the wheelchair through a lever that is easily accessible to the wheelchair occupant, or else automatically through a switch mounted on the wheelchair. In use, the wheelchair is moved to a position such that the drain tube is disposed over a floor drain, and the lever is actuated to open the valve, thereby allowing the urine in the leg bag to empty into the floor drain. When the leg bag is empty, the lever is again actuated to thereby close the valve. This apparatus relies upon gravity to empty the leg bag so that urine can only be emptied into floor located drains or into the ground itself which is unsanitary. In locations which do not have a floor drain, or else the floor drain is not easily accessible, this apparatus cannot be used.

Therefore there is a need for an improved system that allows a person who is confined to a wheelchair and who utilizes a leg bag, or the like, to empty the contents of the leg bag without the assistance of an attendant.

SUMMARY OF THE INVENTION

The present invention provides an improved system that allows a disabled person in a wheelchair to automatically empty the contents of a bodily waste collection receptacle, such as a leg bag, without the aid of an attendant. Since the waste can be emptied without the aid of an attendant, the disabled gains some measure of independence, freedom and privacy, as well as removing a barrier to work, education, etc., and costs are reduced since an attendant is not needed as frequently. Further, the system of the present invention is specifically designed to allow emptying of waste at locations not permitted by conventional systems, thereby further increasing the independence of the disabled person.

In one embodiment in accordance with the invention, a system is provided for emptying bodily waste from a collection receptacle that is carried by an occupant of a wheelchair. The collection receptacle includes a drain tube, and the system comprises a pump having an inlet port and a discharge port, with the inlet port adapted for connection to the drain tube, a discharge line connected to the discharge port of the pump, and means for controlling flow through the discharge line.

In another embodiment in accordance with the invention, a system is provided for emptying urinary waste from a leg bag carried by an occupant of a wheelchair. The leg bag includes a drain tube, and the system comprises a pump mounted on the wheelchair, with the pump having an inlet port and a discharge port. The inlet port is connectable to the drain tube, and a discharge line is connected to the discharge port of the pump. The discharge line is mounted on the wheelchair, and a valve is provided which controls flow through the discharge line. The valve is selectively positionable between an open position in which flow is permitted through the discharge line and a closed position in which flow is prevented through the discharge line.

In yet another embodiment in accordance with the present invention, an improvement to a wheelchair having an electrical power source disposed thereon is provided. The improved wheelchair includes a pump mounted thereon, with the pump having an inlet port and a discharge port. The inlet port is connectable to a receptacle for bodily waste, and the pump is driveable by an electric motor which is electrically connected to the electrical power source. A discharge line is connected to the discharge port of the pump, and the discharge line is moveable relative to the wheelchair. A valve is provided which controls flow through the discharge line, with the valve being operable upon movement of the discharge line relative to the wheelchair.

In still another embodiment in accordance with the present invention, a method of emptying bodily waste from a collection receptacle carried by an occupant of a wheelchair is provided. The collection receptacle includes a drain tube. The method comprises connecting an inlet port of a pump to the drain tube, and connecting a discharge line to a discharge port of the pump, with the discharge line including a valve associated therewith for controlling flow therethrough, where the valve has an open position permitting flow through the discharge line and a closed position preventing flow through the discharge line. The method further comprises actuating the valve to the open position, and activating the pump to thereby pump bodily waste from the collection receptacle and discharge the bodily waste through the discharge line.

A variety of additional advantages of the invention will be set forth in part in the description which follows, and in part will be obvious from the description, or may be learned by practice of the invention. The advantages of the invention will be realized and attained by means of the elements and combinations particularly pointed out in the claims. It is to be understood that both the foregoing general description and the following detailed description are exemplary and explanatory only and are not restrictive of the invention as claimed.

BRIEF DESCRIPTION OF THE DRAWINGS

FIG. 2 is a side view of the valve and discharge line, with the end of the discharge line broken away to illustrate a check valve therein.

FIG. 3 is a top view of the valve and discharge line, showing the discharge line in stowed and operative positions relative to the wheelchair.

DETAILED DESCRIPTION OF THE PREFERRED EMBODIMENT

In the following description of the exemplary embodiment, reference is made to the accompanying drawings which form a part hereof, and in which is shown by way of illustration the specific embodiment in which the invention may be practiced. It is to be understood that other embodiments may be utilized as structural changes may be made without departing from the scope of the present invention.

Generally the system described herein allows a disabled person who utilize a bodily waste collection receptacle, such as a leg bag or the like, and who is confined to a wheelchair, to automatically empty the collection receptacle by themselves, without the aid of an attendant.

Figure 1:
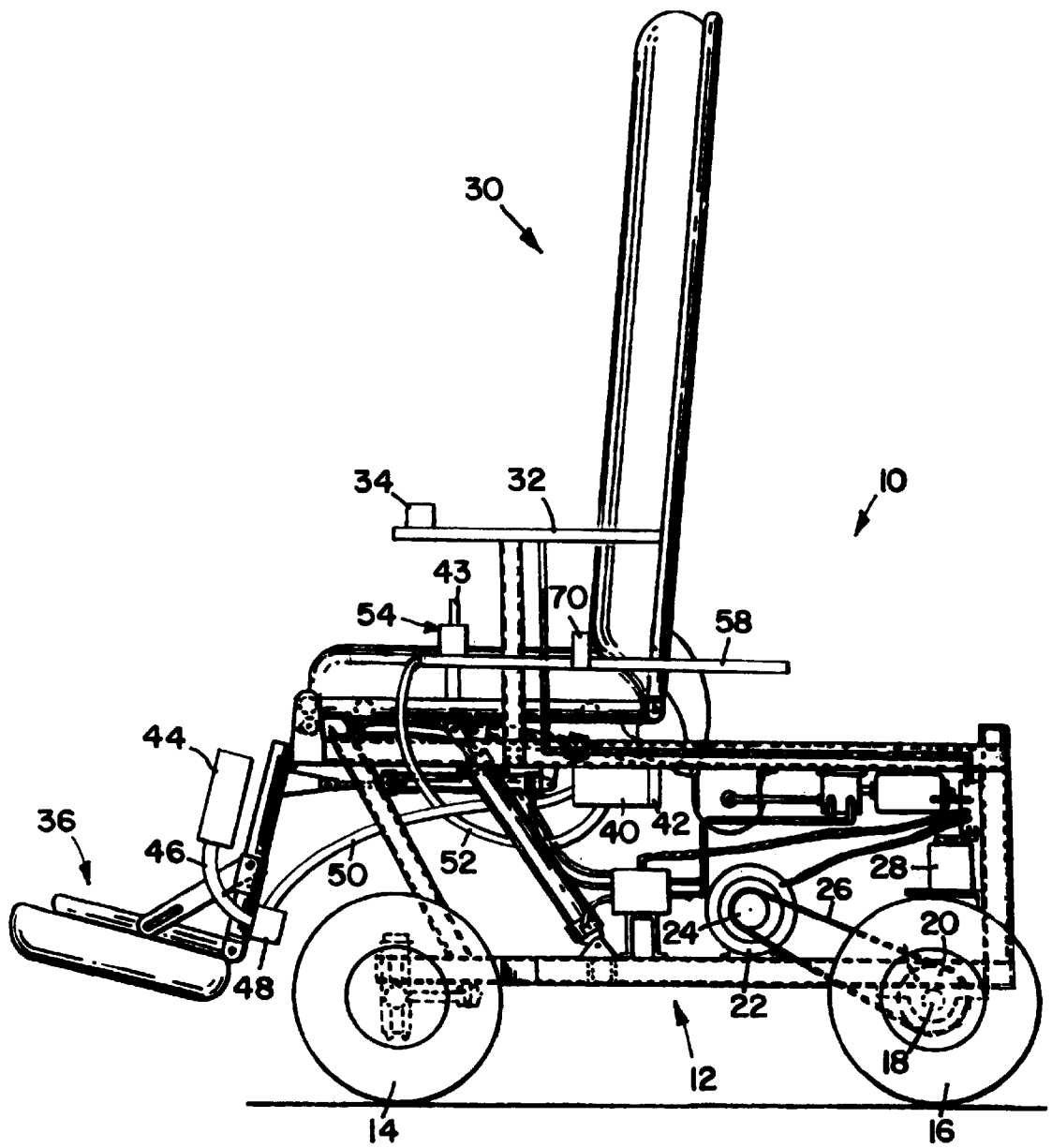
FIG. 1 is a side view of a wheelchair with the components of the system of the present invention mounted thereon.

With reference initially to FIG. 1, a wheelchair 10 suitable for use with the system of the present invention is illustrated. The wheelchair 10 generally includes a rigid framework 12 having a pair of front wheels 14 and a pair of rear wheels 16 connected thereto to enable the wheelchair 10 to roll along the ground. The rear wheels 16 are supported on a common axle 18 having a sprocket 20 fixed thereon. An electric motor 22 is mounted on the framework 12 and drives the rear wheels 16 via a gear mechanism 24 and drive chain 26 which engages the sprocket 20. Electrical power for the motor 22 is provided by a battery 28 that is mounted on the framework 12 and is electrically connected to the motor 22 in suitable fashion. The battery 28 is preferably a 12-volt battery, although the battery could supply higher or lower power if desired.

A seat assembly 30 is mounted on the top of the framework 12 upon which a person sits in use. The seat assembly 30 includes an arm rest 32 on each side thereof upon which the occupant of the wheelchair 10 can rest his/her arms during use. A control box 34 is mounted on one of the arm rests 32 and contains suitable control mechanisms, such as a joystick and switches, for controlling operation of the motor 22 and other equipment associated with the wheelchair 10. Connected to the front end of the framework 12 is a footrest assembly 36, upon which the occupant of the wheelchair places his/her feet during use.

The wheelchair 10 thus far described is a generally typical motorized wheelchair where the rear wheels are driven by an electric motor that is supplied with electrical power by a battery mounted on the wheelchair. The system of the present invention relies upon electrical power provided by the battery 28 on the wheelchair 10 to power a pump that is mounted on the wheelchair, with the pump being used to pump bodily waste, such as urine, from a collection receptacle, e.g. a leg bag, carried by the occupant of the wheelchair. However, it is to be realized that the system of the present invention could be used on a manually powered wheelchair which has a battery mounted thereon to provide power for operating the pump.

Figure 5:
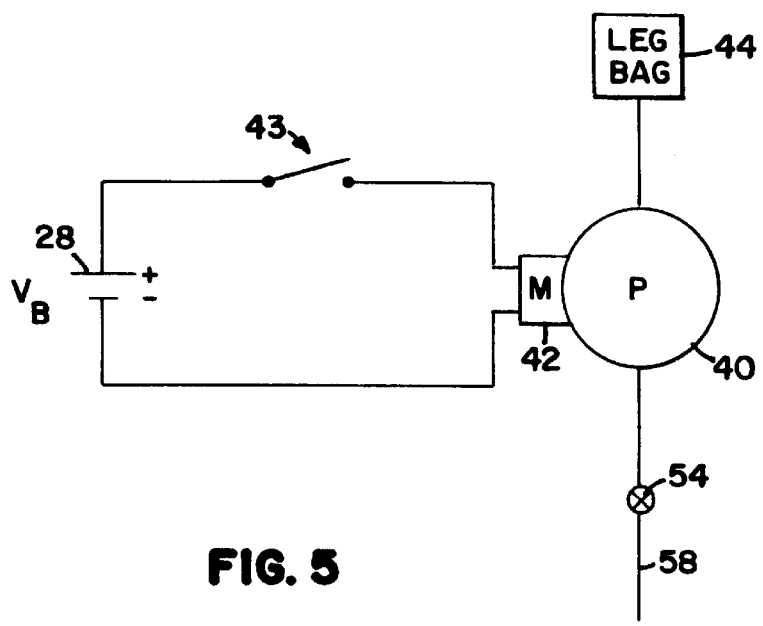
FIG. 5 is a schematic illustration of the electrical connection between the battery on the wheelchair and the motor which drives the pump.

With continued reference to FIG. 1, the system in accordance with the present invention includes a pump 40 that is mounted on the framework 12 of the wheelchair 10, such as underneath the seat assembly 30. The pump 40, which is shown schematically in the figures, is preferably driven by an electric motor 42 that is electrically connected to the battery 28 and which is operable by the electrical power supplied by the battery 28 as can be seen in FIG. 5. The pump 40, which can be a centrifugal or impeller type pump or a positive-displacement type pump, preferably includes an inlet port through which pumped fluid enters and a discharge port through which the pumped fluid is discharged from the pump. Although the pump 40 is described as being driven by an electric motor 42, the pump 40 could be hydraulically driven as well. One type of pump that is suitable for use with the invention is the 402 Series Midi-Fram, Single Piston Diaphragm Pump, made by SHURflo, of Santa Ana, Calif.

The motor 42 for driving the pump 40 is preferably activated by a switch 43 that is mounted at any convenient location on the wheelchair. For instance, as shown in FIG. 1, the switch 43 is mounted on a valve assembly 54 that controls fluid discharged from the pump. The valve assembly 54 is described in detail later in the description. In an alternative embodiment, the switch 43 can be disposed on one of the arm rests 32 of the wheelchair 10, such as on the control box 34 with the other wheelchair controls. The switch 43 can also be mounted at other locations on the wheelchair to allow manual activation thereof by a disabled person, so that the person can activate the pump 40 as desired without the aid of an attendant. A suitable switch for use with the invention is a momentary toggle switch that is spring loaded to the off position.

As described above, a disabled person occupying the wheelchair 10 relies upon a urine collection receptacle 44, commonly referred to as a leg bag, in order to collect urine. The receptacle 44 includes a drain tube 46 at the bottom thereof so that collected urine can be drained from the receptacle. As shown in FIG. 1, a manifold 48 is mounted to the footrest assembly 36 of the wheelchair 10, and the drain tube 46 is connected to an input of the manifold 48. A further tube 50 extends from the manifold 48 to the inlet port of the pump 40. Thus, when the pump 40 is activated, urine is pumped from the receptacle 44, through the drain tube 46, through the manifold 48, through the tube 50, and into the pump. Preferably, the drain tube 46 is connected to the manifold 48 by a quick connect/disconnect coupling to allow the drain tube 46 to be quickly and easily connected/disconnected to the manifold, thereby facilitating transfer of the person into and out of the wheelchair.

A hose 52 extends from the discharge port of the pump 40 to a valve assembly 54 that is mounted on the framework 12 of the wheelchair 10. The hose 52 connects to an inlet 56 of the valve assembly, and a discharge line 58 is connected to an outlet 60 of the valve assembly 54. The valve assembly 54 is preferably selectively positionable to control flow through the discharge line 58. More preferably, the discharge line 58 is moveable relative to the wheelchair 10, and the movement of the discharge line 58 positions the valve assembly 54 such that the position of the discharge line 58 relative to the wheelchair 10 determines the position of the valve assembly 54.

Figure 4:
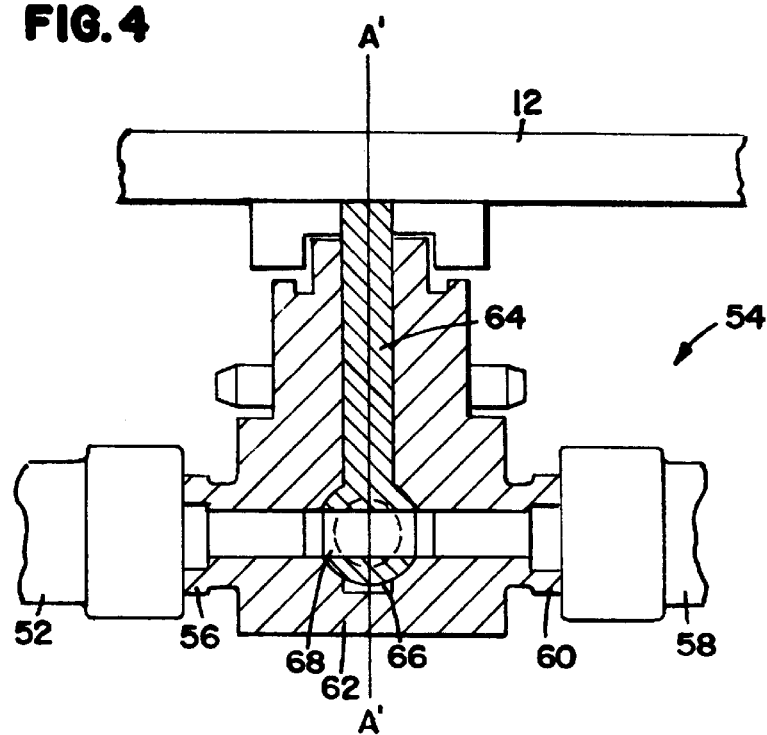
FIG. 4 is a detailed view of the valve which controls flow through the discharge line.

A preferred construction of the valve assembly 54 is illustrated in FIG. 4. The valve assembly 54 is constructed from corrosion resistant material, such as stainless steel and the like, in order to prevent corrosion by the urine and disinfectants that are used to clean the system. The valve assembly 54 includes a valve body 62 defining the inlet 56 and the outlet 60. A valve stem 64 extends through the valve body 62 and is rotatable relative thereto, and a ball 66 or other flow control member is connected to one end of the stem 64 for controlling flow from the inlet 56 to the outlet 60. A passageway 68 is formed through the ball 66 to permit flow between the inlet 56 and the outlet 60 when the passageway 68 is generally aligned with the inlet and outlet, but preventing flow between the inlet and outlet when the passageway 68 is disposed at a right angles to the inlet and outlet. The end of the stem 64 opposite the ball 66 is affixed to the framework 12 of the wheelchair 10 or to a suitable location on the seat assembly 30, such that the valve body 62 is able to rotate relative to the valve stem 64 and ball 66 about the central axis A–A' of the valve assembly 54. A valve assembly that is suitable for use with the present invention is made by the Parker Hannifin Corporation, Instrumentation Valve Division of Jacksonville, Ala. Although the valve assembly 54 is shown and described as being a ball valve type, other types of valve assemblies can be used if desired, such as a plug valve and the like.

As mentioned previously, the discharge line 58 is connected to the outlet 60 of the valve body 62. Thus, the discharge line 58 can be rotated relative to the wheelchair 10 about an axis coinciding with the axis A–A' of the valve assembly 54, thereby causing the valve body 62 to rotate relative to the valve stem 64. Thus, the position of the discharge line 58 relative to the wheelchair 10 determines the operating position of the valve assembly 54, thereby controlling flow through the valve assembly and into the discharge line. The valve body 62, valve stem 64, ball 66 and passage 68 are preferably arranged to have a closed configuration at one position of the discharge line 58 relative to the wheelchair 10 thereby preventing flow through the valve assembly 54, and to have an open configuration at a second position of the discharge line relative to the wheelchair to allow flow through the valve assembly and into the discharge line.

As illustrated in FIG. 3, the discharge line 58 is moveable through an arc of ninety degrees between a first, stowed position (shown in dashed lines) generally against the wheelchair 10 and a second, operative position (shown in solid lines) at which the discharge line extends outward from the wheelchair 10 generally at a ninety degree angle. At the first, stowed position of the discharge line 58, the valve assembly is in the closed configuration to prevent flow therethrough. At the second, operative position of the discharge line 58, the valve assembly has been actuated to the open configuration, thereby allowing flow through the valve assembly and into the discharge line. Therefore, the pump 40 is not able to pump urine from the receptacle 44 to the discharge line 58 for emptying the receptacle until the discharge line has been rotated about ninety degrees to the second, operative position. This is a precautionary measure in the event that the motor 40 is inadvertently activated, such as by accidentally actuating the switch 43.

With reference to FIGS. 1–3, to facilitate rotation of the discharge line 58, an actuating block 70 is fixed to the discharge line 58. The block 70 allows a disabled person lacking finger movement to rotate the discharge line 58. Further, as shown in FIG. 2, a distal end of the discharge line 58 includes a check valve 72 disposed therein. The check valve 72 prevents leakage of urine from the discharge line 58, and permits flow through the discharge line 58 only when a sufficient pressure is generated by the pump 40.

The discharge line 58 is preferably made to be flexible to allow it to be bent up and down, as shown in dashed lines in FIG. 2, and side to side, as shown in dashed lines in FIG. 3, and is made from semi-rigid materials to remain in its bent configuration until it is bent back to its original shape. In a preferred embodiment, the discharge line 58 comprises an inner tube made from a corrosion-resistant, flexible, polymeric material, such as TEFLON® or SANTOPRENE®, surrounded by a semi-rigid, flexible metallic tube that is encased in flexible polyvinyl chloride (PVC). The inner tube carries the pumped fluid therethrough and must be resistant to the corrosive effects of the urine as well as the disinfectants that are used to clean the system. The semi-rigid, flexible metallic tube permits the discharge line 58 to be bent to a particular shape and maintains the discharge line at its bent shape until it is bent to another shape.

Quick connect/disconnect couplings can be used to secure the tube 50 to the inlet port of the pump 40, to secure the tube 52 to the outlet port of the pump 40 and to the inlet 56 of the valve assembly 54, and to secure the discharge line 58 to the outlet 60 of the valve assembly 54, to thereby facilitate maintenance and repair operations on the system.

In use of the system, after the drain tube 46 of the receptacle 44 has been connected to the manifold 48 and with the pump 40 initially off, the person positions the wheelchair adjacent to a toilet, urinal or other similar drain into which the urine is to be discharged. The discharge line 58 is then manually rotated to the operative position extending about 90 degrees outward from the wheelchair, facilitated by the block 70 connected to the discharge line 58. The movement of the discharge line to the operative position actuates the valve assembly to the open position to allow flow from the pump 40 and through the discharge line. If need be, the discharge line 58 is appropriately bent to ensure that the urine is discharged into the toilet or urinal. Once the discharge line is positioned properly, the person activates the switch 43, thereby turning on the pump 40 which pumps urine from the receptacle 44, through the drain tube 46, manifold 48, tubes 50, 52, the valve assembly 54 and the discharge line 58 and into the toilet or urinal. The check valve 72 located in the end of the discharge tube 58 prevents urine leakage between the time that the discharge line is rotated to open the valve assembly 54 and the time that the switch 43 is activated.

Once the receptacle 44 is empty, or when the person decides to stop emptying of the receptacle, the person merely releases the switch 43, thereby turning off the pump 40. The check valve 72 will then close, preventing any further urine from being discharge from the discharge line. The discharge line 58 is then rotated back to the stowed position, thereby closing the valve assembly 54 to ensure that accidental activation of the pump 40 does not cause further urine to be discharged.

The system of the present invention thus allows a disabled person to empty a urine receptacle without the aid of an attendant. Further, the design of the system allows the urine to be discharged into ordinary toilets and urinals, as well as into floor drains.

While the system has been described as being used on a motorized wheelchair, the system could also be used on manually powered wheelchairs used by disabled persons who have use of their arms. In this case, a battery or other suitable supply of power would need to be mounted on the wheelchair for the specific purpose of powering the pump. Further, although the switch has been shown and described as being mounted on the valve assembly, the switch could be located in any position that would allow activation by the person in the wheelchair, such as on one of the arm rests.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A system for emptying bodily waste from a collection receptacle that is carried by an occupant of a wheelchair, the collection receptacle including a drain tube, comprising in combination:

a wheelchair;

a pump mounted on the wheelchair, said pump having an inlet port and a discharge port, the inlet port adapted for connection to the drain tube;

a discharge line connected to the discharge port of said pump, said discharge line being moveably mounted on the wheelchair whereby said discharge line is moveable relative to the wheelchair; and means for controlling flow through the discharge line.

2. The system according to claim 1, wherein the pump is electrically driven, and the pump is electrically connected to an electrical power source disposed on the wheelchair.

3. The system according to claim 2, further including a switch for controlling flow of electricity to the pump and thereby controlling operation of the pump.

4. The system according to claim 3, wherein said switch is mounted on the wheelchair.

5. The system according to claim 1, wherein the means for controlling flow comprises a valve.

6. The system according to claim 5, wherein the valve is operable upon relative movement between said discharge line and the wheelchair.

7. The system according to claim 6, further including an actuating block secured to said discharge line to facilitate movement of the discharge line relative to the wheelchair.

8. The system according to claim 1, wherein the discharge line is flexible.

9. A system for emptying urinary waste from a leg bag carried by an occupant of a wheelchair, the leg bag including a drain tube, comprising in combination:

a wheelchair;

a pump mounted on the wheelchair, said pump having an inlet port and a discharge port, and said inlet port connectable to the drain tube;

a discharge line connected to said discharge port of said pump, said discharge line being moveably mounted on the wheelchair whereby said discharge line is moveable relative to the wheelchair; and a valve controlling flow through the discharge line, said valve being selectively positionable between an open position in which flow is permitted through the discharge line and a closed position in which flow is prevented through the discharge line.

10. The system according to claim 9, wherein the pump is electrically driven, and the pump is electrically connected to an electrical power source disposed on the wheelchair.

11. The system according to claim 10, further including a switch for controlling flow of electricity to the pump and thereby controlling operation of the pump.

12. The system according to claim 11, wherein said switch is mounted on the wheelchair.

13. The system according to claim 9, wherein the valve is operable upon relative movement between said discharge line and the wheelchair.

14. The system according to claim 13, further including an actuating block secured to said discharge line to facilitate movement of said discharge line relative to the wheelchair.

15. The system according to claim 13, wherein said discharge line is moveable about an axis over an arc of about ninety degrees.

16. The system according to claim 15, wherein the axis of movement of said discharge line coincides with a central axis of said valve.

17. The system according to claim 15, wherein said discharge line includes a first position relative to the wheelchair, and said valve being in the closed position at the first position of said discharge line, and said discharge line includes a second position relative to the wheelchair, and said valve being in the open position at the second position of said discharge line.

18. The system according to claim 9, wherein the discharge line is flexible.

19. The system according to claim 9, wherein said discharge line includes a distal end, and further including a check valve disposed in said discharge line adjacent the distal end thereof.

20. In a wheelchair having an electrical power source disposed thereon, the improvement comprising:

a pump mounted on the wheelchair, said pump having an inlet port and a discharge port, and said inlet port connectable to a receptacle for bodily waste, said pump being driveable by an electric motor, and said electric motor is electrically connected to the electrical power source;

a discharge line connected to said discharge port of said pump, said discharge line being moveable relative to the wheelchair; and a valve controlling flow through the discharge line, said valve being operable upon movement of said discharge line relative to the wheelchair.

21. A method of emptying bodily waste from a collection receptacle carried by an occupant of a wheelchair, the collection receptacle including a drain tube, comprising:

mounting a pump on the wheelchair, the pump having an inlet port and a discharge port;

moveably mounting a discharge line on the wheelchair so that the discharge is moveable relative to the wheelchair;

connecting the inlet port of the pump to the drain tube;

connecting said discharge line to the discharge port of the pump, the discharge line including a valve associated therewith for controlling flow therethrough, the valve having an open position permitting flow through the discharge line and a closed position preventing flow through the discharge line;

actuating the valve to the open position; and activating the pump to thereby pump bodily waste from the collection receptacle and discharge the bodily waste through the discharge line.

22. The method according to claim 21, wherein the step of actuating the valve comprises moving the discharge line relative to the wheelchair.

23. The method according to claim 21, wherein the step of activating the pump comprises actuating a switch that is mounted on the wheelchair.

* * * * *